United States Patent
Davydov et al.

(10) Patent No.: US 9,150,466 B2
(45) Date of Patent: Oct. 6, 2015

(54) COUNTER-CURRENT FLUIDIZED BED REACTOR FOR THE DEHYDROGENATION OF OLEFINS

(71) Applicant: UOP LLC, Des Plaines, IL (US)

(72) Inventors: Lev Davydov, Northbrook, IL (US); Wolfgang A. Spieker, Glenview, IL (US); Paolo Palmas, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/681,914

(22) Filed: Nov. 20, 2012

(65) Prior Publication Data

US 2014/0142362 A1 May 22, 2014

(51) Int. Cl.
*C07C 5/327* (2006.01)
*C07C 5/333* (2006.01)
*C07C 5/32* (2006.01)
*C10G 49/00* (2006.01)

(52) U.S. Cl.
CPC ............. *C07C 5/327* (2013.01); *C07C 5/333* (2013.01); *C10G 49/00* (2013.01); *C10G 49/002* (2013.01); *C10G 2300/1081* (2013.01); *C10G 2400/20* (2013.01); *C10G 2400/22* (2013.01)

(58) Field of Classification Search
CPC .......... C07C 5/327; C07C 5/333; C07C 5/32; C07C 5/321
USPC .......................................................... 585/659
See application file for complete search history.

(56) References Cited

U.S. PATENT DOCUMENTS

| | | | | |
|---|---|---|---|---|
| 5,214,225 A * | 5/1993 | Hall et al. | | 585/654 |
| 5,254,788 A * | 10/1993 | Gartside et al. | | 585/659 |
| 6,166,282 A | 12/2000 | Miller | | |
| 6,403,854 B1 | 6/2002 | Miller | | |
| 7,235,706 B2 * | 6/2007 | Iezzi et al. | | 585/654 |
| 2011/0319692 A1 * | 12/2011 | Spieker et al. | | 585/659 |

OTHER PUBLICATIONS

U.S. Appl. No. 13/681,945, filed Nov. 20, 2012, Davydov et al.

* cited by examiner

*Primary Examiner* — In Suk Bullock
*Assistant Examiner* — Youngsul Jeong

(57) ABSTRACT

A process and apparatus for the dehydrogenation of paraffins is presented. The process utilizes a reactor that includes a slower flow of catalyst through the reactor, with a counter current flow of gas through the catalyst bed. The catalyst is regenerated and distributed over the top of the catalyst bed, and travels through the bed with the aid of reactor internals to limit backmixing of the catalyst.

19 Claims, 6 Drawing Sheets

COUNTER-CURRENT FLUIDIZED BED REACTOR FOR THE DEHYDROGENATION OF OLEFINS

FIELD OF THE INVENTION

The field of the invention is production of light olefins. In particular, the invention relates to the dehydrogenation of paraffins in the C3 to C5 range.

BACKGROUND OF THE INVENTION

Ethylene and propylene are light olefin hydrocarbons with two or three atoms per molecule, respectively, are important chemicals for use in the production of other useful materials, such as polyethylene and polypropylene. Polyethylene and polypropylene are two of the most common plastics found in use today and have a wide variety of uses for both as a material fabrication and as a material for packaging. Other uses for ethylene and propylene include the production of vinyl chloride, ethylene oxide, ethylbenzene and alcohol. Steam cracking or pyrolysis of hydrocarbons produces essentially all of the ethylene and propylene. Hydrocarbons used as feedstock for light olefin production include natural gas, petroleum liquids, and carbonaceous materials including coal, recycled plastics or any organic material.

A light olefin plant is a very complex combination of reaction and gas recovery systems. The feedstock is charged to a cracking zone in the presence of steam at effective thermal conditions to produce a pyrolysis reactor effluent gas mixture. The pyrolysis reactor effluent gas mixture is stabilized and separated into purified components through a sequence of cryogenic and conventional fractionation steps. A typical light olefin plant includes an ethylene separation section containing both cryogenic and conventional fractionation steps to recover an ethylene product with a purity exceeding 99.5% ethylene. Propylene and heavier hydrocarbons are separated from the ethylene and recovered in a separate section, or separate fractionation column.

Modification of the process can save energy, and equipment which are very expensive, while increasing the overall yields of product.

SUMMARY OF THE INVENTION

The present invention is a process for the dehydrogenation of hydrocarbons. In particular, the present invention is for a gas phase conversion of alkanes in the C2 to C5 range to olefins. The process includes using a vessel having a large diameter for flowing a catalyst downward through a catalyst bed. The process includes flowing a gas phase hydrocarbon process stream upward through the catalyst bed to dehydrogenate the hydrocarbons as the process stream contacts the catalyst. The catalyst is passed to the reactor to a region above the catalyst bed at a temperature of at least 600° C. The process stream is passed to the reactor at a temperature less than 600° C.

The process involves the counter-current flow of catalyst with respect to the process stream, and the process stream picks up heat from the catalyst as it contacts the catalyst during the endothermic reaction of dehydrogenation. A temperature gradient is formed within the catalyst bed with the top of the catalyst bed at or near the highest temperature and the bottom of the catalyst bed at or near the lowest temperature. It is preferred to have a temperature difference between the process stream inlet temperature and the catalyst inlet temperature, wherein the catalyst is at least 50° C. hotter than the process stream temperature.

Other objects, advantages and applications of the present invention will become apparent to those skilled in the art from the following detailed description and drawings.

DETAILED DESCRIPTION OF THE INVENTION

Currently, the production of light olefins is primarily from the normal sources of light olefins that are produced through the cracking process of naphtha and heavier hydrocarbons, and through the process of cracking heavier olefins. Light olefins are subsequently separated out from a product stream comprising ethylene and propylene. There is a growing gap between the production of light olefins and the demand for these polymer building blocks. The demand is being met through dedicated processes that use light paraffinic feedstocks, and directly convert the paraffins to olefins through dehydrogenation. One example of a preferred feedstock is propane or an LPG feed. This can be directly dehydrogenated and overcomes drawbacks of other methods of propylene production, such as methanol to olefins and the cracking of heavier hydrocarbons.

Figure 1:
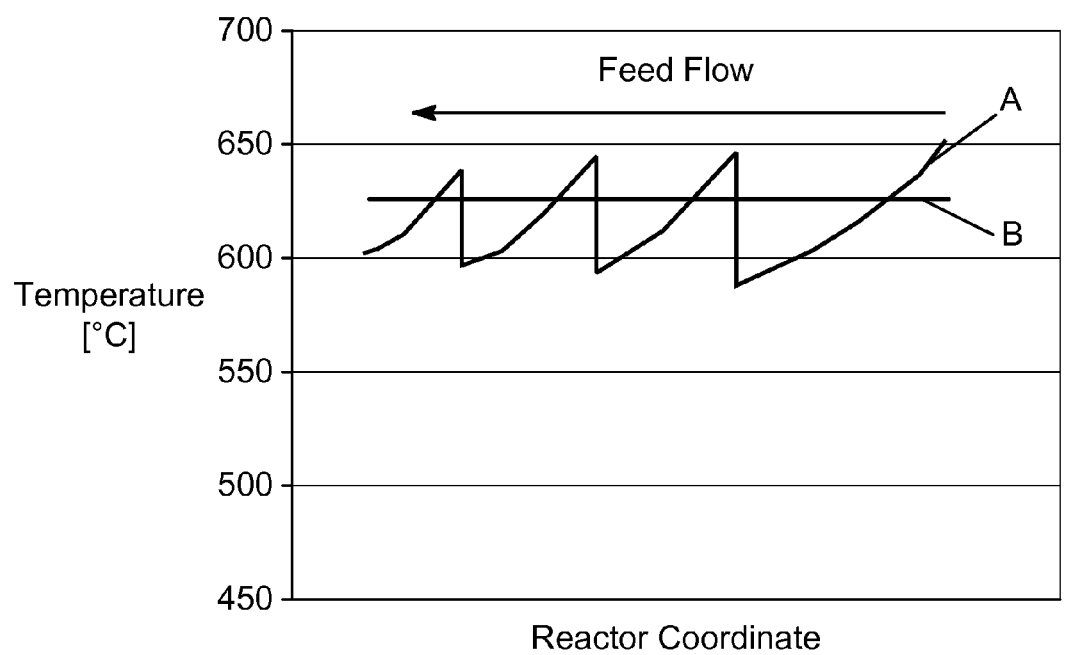
FIG. 1 is a plot of a process stream temperature for a typical process utilizing multiple reactors.

The production of light olefins using a process for the direct conversion of a paraffin feedstream to the olefin analog utilizes a noble metal catalyst. The challenges in dehydrogenation technology include the reaction conditions, such as pressure and temperature, that favorably shift the dehydrogenation equilibrium towards olefins, and the large amount of heat required to drive the reaction, while minimizing undesirable side reactions, such as non-selective thermal conversion. The dehydrogenation process is endothermic, and currently the process utilizes a plurality of reactor beds with interstage heating between the reactor beds. As shown in FIG. 1, the process comprises heating the feed to each reactor, where the process stream cools due to the endothermicity.

In one operation (A), the process stream as it exits one reactor is reheated and passed to a subsequent reactor and cools again. This process is repeated several times with a balance achieved between the number of reactors and the extent of conversion. The process stream is cycled several times through interreactor heaters to bring the temperature back to a design inlet temperature. The process with multiple reactors wherein the reactors are run until the temperature of the catalyst has dropped to a level where the conversion is too low to continue. The catalyst would then be withdrawn and reheated. This is controlled by controlling the flow of catalyst through the reactor. The utilization of multiple reactors balances the reheating of the catalyst and process stream with the length of contact time of the process stream at a high temperature, and allowances for the cooling due to the endothermicity. A second process (B) utilizes a large, back-mixed, reactor to generate a substantially uniform temperature in the reactor, with heat continuously added through the addition of fresh heated catalyst. The second process exposes the process stream to extended periods of high temperatures.

The use of multiple reactors requires the use of hot transfer lines, and extra heaters. This increases the lengths of time the process stream is at a high temperature, and can contribute to cracking, and reactions between the process stream and hot metal in the equipment. This is overcome with a new approach to reduce the need to a single reactor and minimized the high temperature contact times, which in turn minimizes thermal cracking.

The new approach is to utilize a counter-current flow process for contacting the paraffin with the catalyst. The new process utilizes a larger reactor, and allows for a larger gas flow rate, but has a lower catalyst flux. The catalyst is controlled to flow downward while contacting the gas flowing upward in the reactor. The catalyst can be kept in the reactor for a longer residence time where the catalyst can be allowed to cool more. There is an increase in yields while decreasing the contact time between the process stream and the catalyst at the relatively high temperatures where undesired side reactions can occur. The catalyst residence time is determined by several factors, including the choice of catalyst.

This process is amenable to using a catalyst having a relatively short life before regeneration is required. For a short lived catalyst, such as zirconia, the residence time can be between 10 seconds and 20 minutes. For a catalyst having a longer life between regeneration, such as a noble metal catalyst on a support, the residence time can be up to several days.

Figure 2:
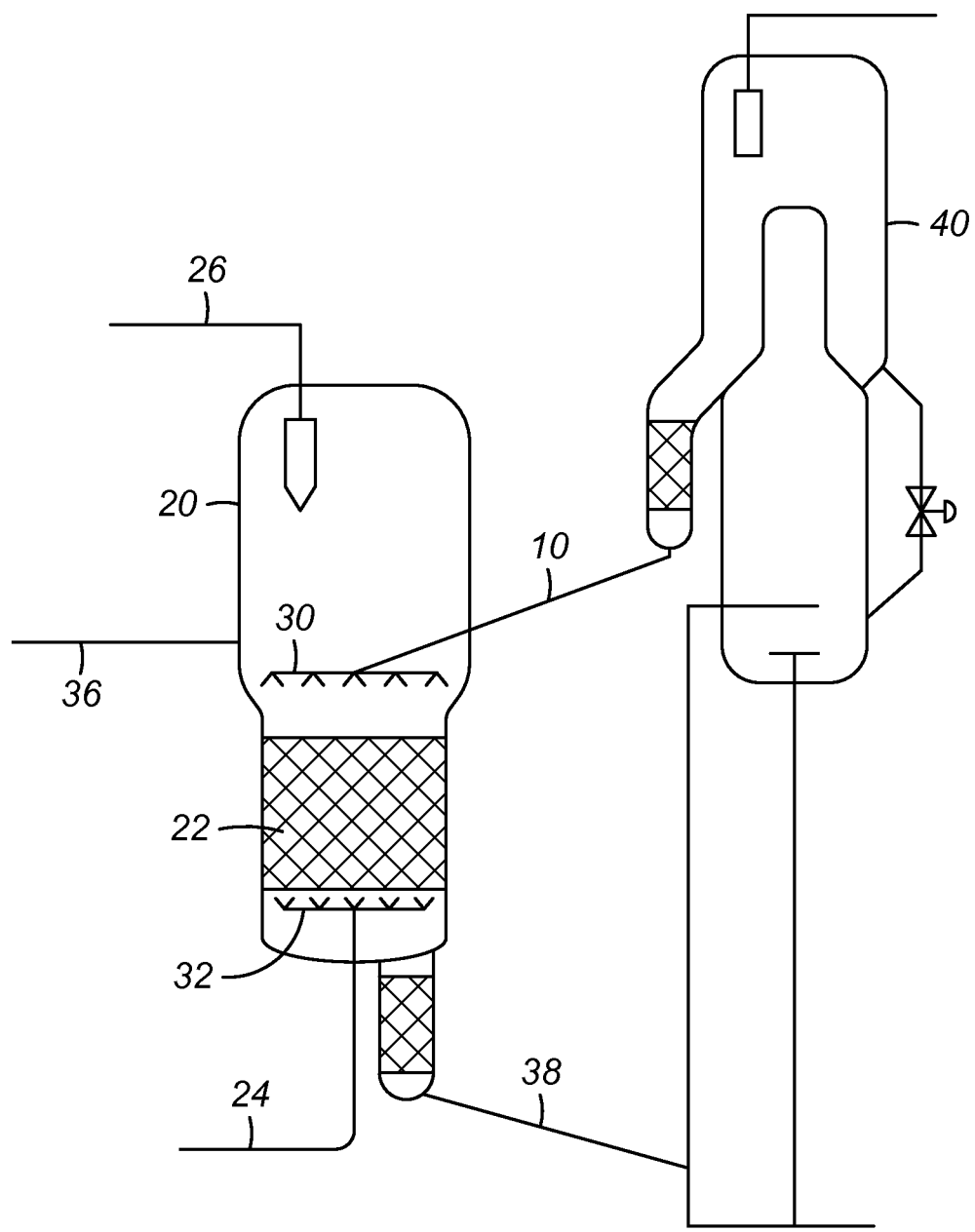
FIG. 2 is a schematic of the design for a dehydrogenation system including reactor and regenerator system.

The process is for the dehydrogenation of propane and butane, and gives an improvement over current processes. The process, as shown in FIG. 2 returns a regenerated catalyst stream 10 to a dehydrogenation reactor 20. The catalyst flows downward through a catalyst bed 22 in the reactor 20. A paraffinic feedstream 24 is passed to the reactor 20 and flows in an upward direction through the catalyst bed 22, thereby contacting the feedstream and catalyst at dehydrogenation reaction conditions, to generate a product stream 26 comprising olefins. Spent catalyst is collected at the bottom of the reactor 20 and transferred through a catalyst transfer line 38 and passed to a regenerator 40. The regenerator 40 regenerates the catalyst and returns the regenerated catalyst stream 10 to the reactor 20. The regenerated catalyst can undergo a stripping process with an inert gas to remove residual combustion products from the regenerator. The inert gas can also be heated to maintain the catalyst temperature and to facilitate desorption of adsorbed combustion products.

In the present invention, the dehydrogenation process includes a reaction temperature between 400° C. and 800° C., with the temperature gradient along the axial direction of the reactor. The reactor is at its highest temperature at the top with the inlet of the regenerated catalyst and cools as the catalyst proceeds through the reactor. The catalyst feed is introduced to the reactor at a temperature of at least 600° C., but less than 800° C. A preferred catalyst feed temperature is between 650° C. and 750° C., with a more preferred catalyst feed temperature between 670° C. and 730° C.

The process is counter current, so the paraffinic feed, or process stream, is introduced at the bottom, or where the temperature is at its lowest. The paraffinic feed is introduced at a temperature no greater than 600° C., with the feed temperature of the process stream at least 400° C. A preferred paraffinic feed stream temperature is between 450° C. and 550° C. and partial conversion is achieved at the relatively low temperature. A more preferred paraffinic feed temperature is between 470° C. and 520° C.

Figure 3:
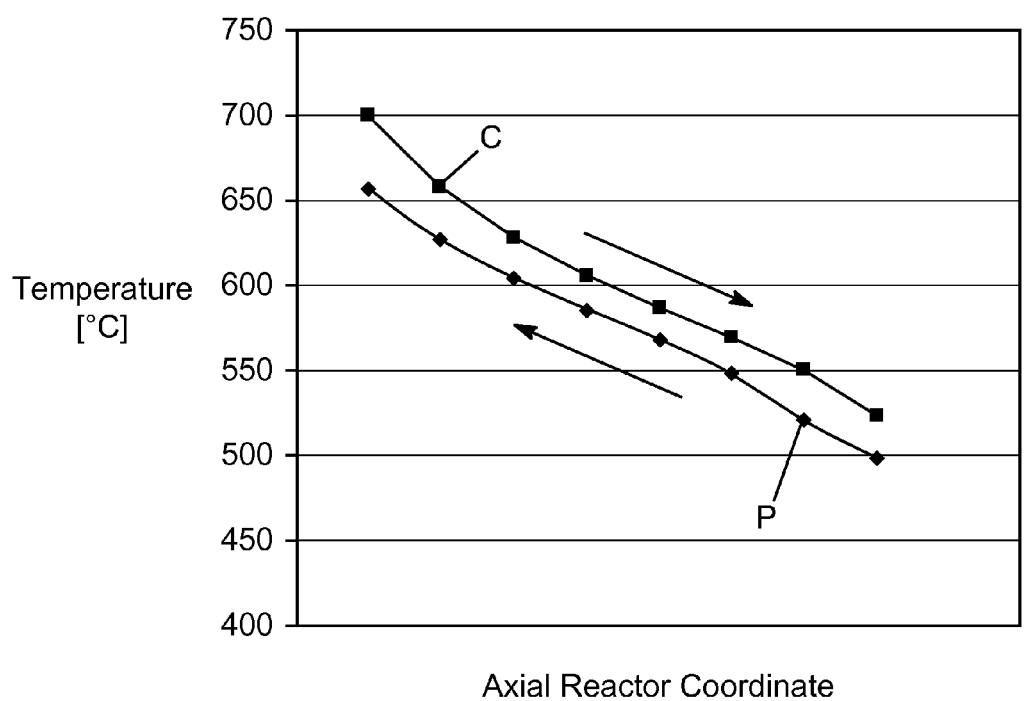
FIG. 3 is a plot of the process stream temperature for the counter-current flow.

This significantly reduces the amount of cracking of the hydrocarbons in the process stream, by achieving some conversion at low temperatures. The equilibrium is shifts as the reaction proceeds, and to continue to drive the reaction the temperature needs to be increased to shift the equilibrium in a favorable direction. By passing the process stream counter current to the catalyst, the equilibrium adjusts favorably as the reaction proceeds and the process stream is exposed to an increasing temperature as it passes through the reactor. The temperature profiles of the catalyst and feed are shown in FIG. 3, and are established through control of the flow of catalyst (C) and the process stream (P). The larger catalyst bed provides the heat for the reaction with the catalyst cooling as it moves downward, and allowing for initial conversion in the feedstream at a lower temperature. While the profiles shown on FIG. 3 appear to have the process stream at a different temperature than the catalyst, the figure is showing the temperatures as the material, either process stream or catalyst, enters a theoretical stage. The points adjacent on the line would be the temperatures of the material either leaving one stage, or entering an adjacent stage. The lines, (C) and (P), will in actuality more closely overlay each other, or the lines will be shifted relative to each other to the left or right in the figure until a portion of the lines are overlaid. For example, the second point on the line (from the left) for the catalyst flow line would have a close temperature to the first point of the line (from the left) for the process stream. These would be the temperatures of the material leaving the upper theoretical stage.

The overall hot residence time is significantly reduced, and the process stream is exposed to high temperature only in the presence of catalyst for the short period of time as the process stream exits the catalyst bed. The highest temperature exposure of the process stream is also for the short contact time at the end of the process streams residence in the reactor. The reaction conditions also include a reactor outlet pressure between 20 kPa (absolute) and 400 kPa (absolute). Preferred reactor outlet pressures are from 105 kPa (absolute) to 300 kPa (absolute), with alternate operating conditions for the reactor outlet pressure between 110 kPa (absolute) and 250 kPa (absolute), and between 120 kPa (absolute) and 200 kPa (absolute).

The process further includes cooling the product stream 26. The product stream can be passed through a combined feed heat exchanger to preheat the paraffinic feed stream, and cool the product stream. The process can include passing a portion of the cooled product stream to the upper region of the reactor 20 through a quench line 36. The cooled portion of the product stream quenches the process stream as it comes off the catalyst bed. The quenching inhibits further undesired side reactions due to the high temperatures, by rapidly cooling the process stream.

The process seeks to provide a substantially uniform distribution of catalyst across the catalyst bed for flowing down through the reactor. The catalyst returning from the regenerator 40 is passed to a catalyst distributor 30 to provide for the uniform distribution of regenerated catalyst over the bed. The process also seeks to maintain a uniform distribution of the process stream flowing up through the catalyst bed. The paraffinic feed stream is passed to a feed distributor 32 to provide a substantially uniform distribution of the feed stream across the catalyst bed.

An aspect of the invention is to maintain a substantially uniform temperature difference between the catalyst and the process stream as the catalyst and process stream flow through the reactor. The catalyst provides the heat to drive the endothermic reaction, and as the reaction proceeds, the catalyst is cooled and flows downward. The reactants flow upward and are exposed to an increasing temperature to provide the heat for the reaction, and to heat the process stream.

The process includes passing catalyst to the reactor at a catalyst inlet temperature of at least 600° C., and preferable at least 650° C. The catalyst is distributed over the top of the catalyst bed and flows downward through the reactor. The process includes passing a paraffinic feed stream to a distributor disposed beneath the catalyst bed. The feed stream flows upward through the catalyst bed. The feed stream is passed to the reactor at a temperature of at least 50° C. below the catalyst inlet temperature. To maintain the temperature difference between the catalyst and the process stream, it is preferred that the paraffinic feed stream inlet temperature is between 100° C. and 250° C. below the catalyst inlet temperature, with a more preferred range of inlet temperature differences between 150° C. and 200° C. The control of the temperature differences is partially dependent upon the catalyst flow rates through the reactor and the process stream flow rates through the reactor.

Figure 4:
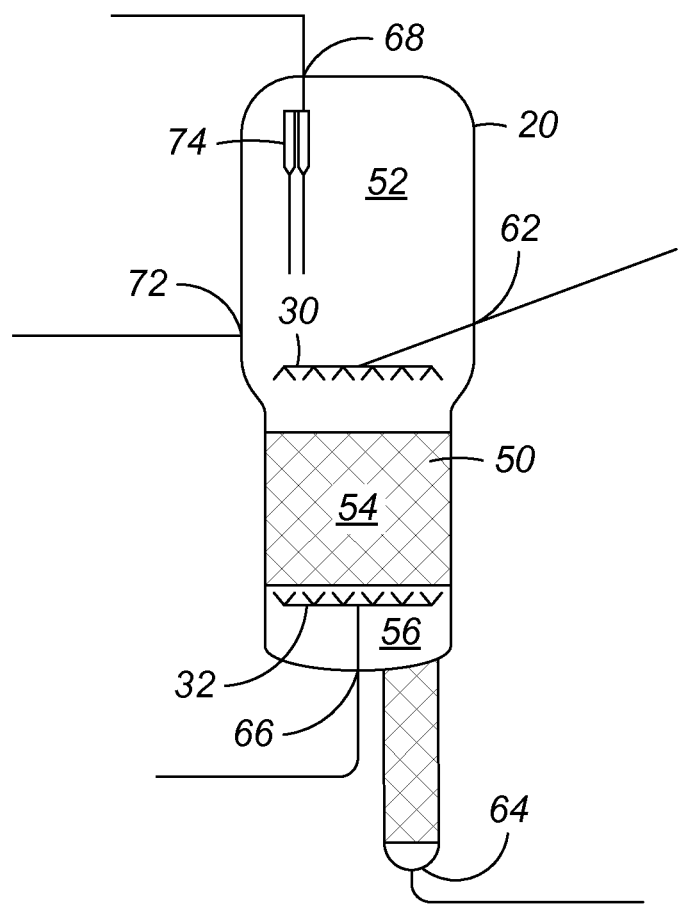
FIG. 4 is a diagram of the reactor.

An aspect of the invention is the apparatus for the dehydrogenation of hydrocarbons. The apparatus comprises a large reactor 20, as shown in FIG. 4. The reactor 20 can be a larger diameter reactor, up to 11 meters, with a preferred range from 6 to 10 meters. This allows for a higher gas flow rate, while having a lower catalyst flux within the reactor. Gas flow rates within the reactor are preferred to be from 0.4 m/s to 1 m/s, with catalyst flux rates around 100,000 kg/m2/hr. The catalyst is distributed over the reactor bed with a catalyst distributor 30, and the paraffin feedstream is distributed across the bottom of the catalyst bed through a gas distributor 32. The reactor can include packing grids 50, or other reactor internals for guiding the catalyst in the downward direction and for reducing and limiting and axial back-mixing of the catalyst. Other reactor internals for this purpose include stripper trays such as used in an FCC unit, or gratings, provided the counter-current flow of catalyst and gas can be established with limited or no axial backmixing.

The reactor 20 comprises a reactor shell having an upper region 52, a central region 54 and a lower region 56. A catalyst inlet 62 is disposed in the upper region 52 of the shell, a catalyst outlet 64 disposed in the lower region 56 of the shell, a process stream inlet 66 is disposed in the lower region 56 of the shell, and a product stream outlet 68 is disposed in the upper region of the shell. The reactor 20 further includes a set of reactor internals 50 disposed within the central region 54 of the shell, wherein the reactor internals 50 limit axial back-mixing of the catalyst.

The reactor design is for limiting the times the process stream is exposed to high temperatures. The reactor 20 includes a quench port 72 disposed in the upper region 52 of the reactor shell. The quench port 72 is for admitting a portion of the cooled product stream to rapidly reduce the product temperature. The quench port can include a distributor for rapidly dispersing a cooled quench fluid into the upper region 52 of the reactor.

The central region 54 of the reactor holds the reactor internals 50 and the catalyst flowing through the reactor. The central region 54 provides for a substantially uniform flow of catalyst, and has an axial length to diameter (L/D) ratio between 0.5 and 5, with a preferred length to diameter ratio between 0.6 and 2, and with a more preferred length to diameter ratio between 0.8 and 1.2. The axial length is the depth of the catalyst bed, including reactor internals, for the reactor.

The central region 54 includes reactor internals that comprise a structured packing material. The structured packing includes a plurality of ribbons, where each ribbon is angled, relative to the central axis of the reactor vessel 20. The ribbons refer to metal strips formed and angled relative to each other. The ribbons are arranged in arrays with a plurality of ribbons forming a layer. The packing can include multiple layers of the ribbons. With multiple layers, each layer of ribbons can be rotated around the central axis relative to each other to provide for axial and azimuthal mixing of the catalyst. The neighboring layers, or neighboring packing units, are stacked to be in contact with neighboring units. The units are preferably affixed to one another, or are stacked with small spacers. Neighboring packing units are preferably rotated relative to each other around the central axis of the vessel. The amount of rotation is between 30° and 150° relative to a neighboring unit, and preferably between 80° and 100°, and most preferably rotated at a 90° angle.

Each layer is attached to a neighboring layer, either through welding, or with mechanical items to affix the layers together, including rivets, screws, and other appropriate hardware. The ribbons can partially obstruct the passage of catalyst particles, and the angled portion provides movement of the catalyst in either the radial direction, azimuthal direction, or a combination of both directions. For purposes of this invention, the movement in the radial direction refers to radial movement toward or away from the central axis of the vessel;

the movement in the azimuthal direction is movement around the central axis of the vessel; and axial movement is movement parallel to the central axis of the vessel.

Figure 5:
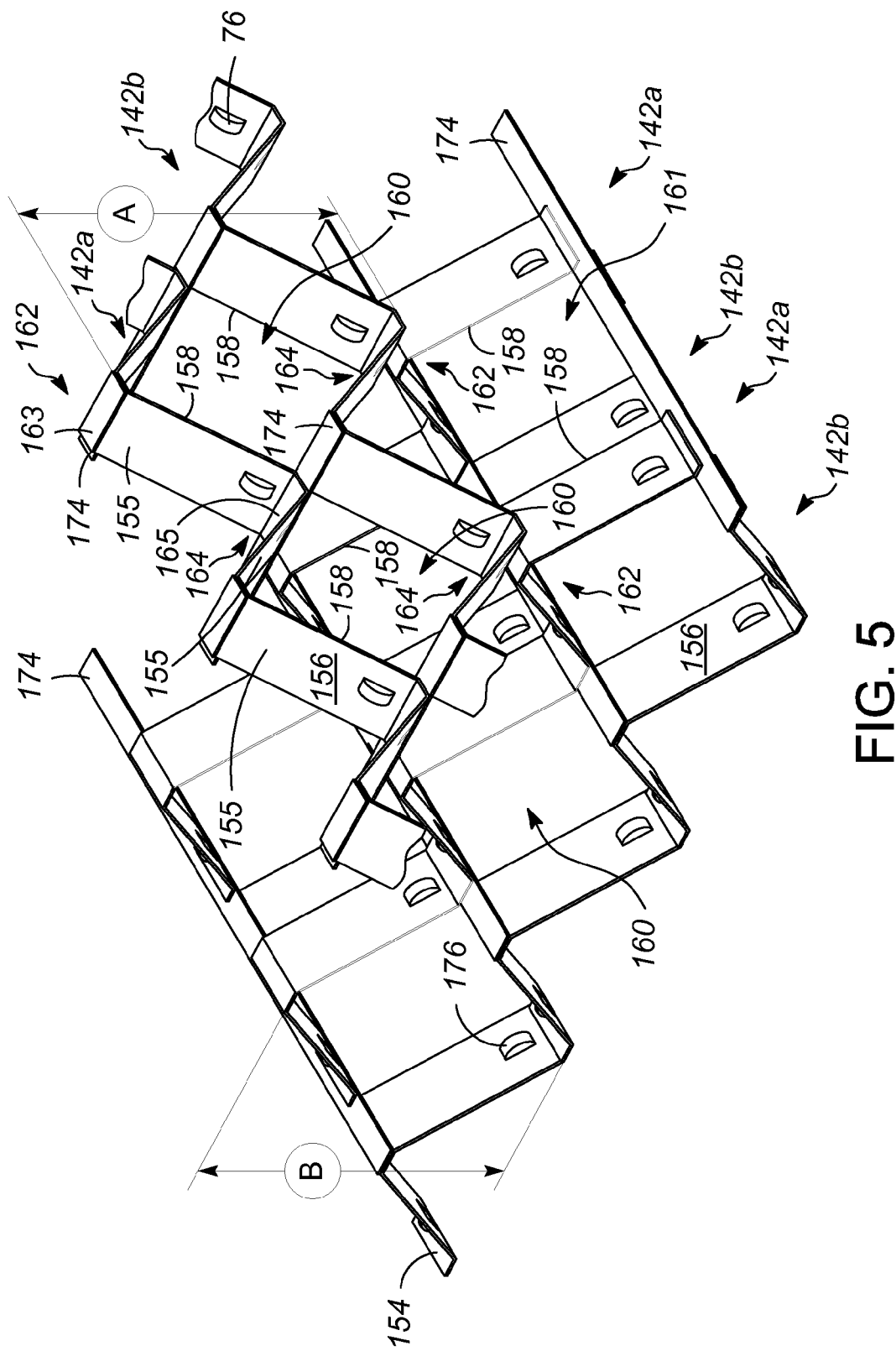
FIG. 5 shows one example of the reactor internals.

An enlarged view of two layers A, B of the structural packing 50 is shown in a perspective view in FIG. 5. Each ribbon 142a,b comprises bands 154 configured in undulating peaks 162 and valleys 164. Each band 154 includes a face 156 that obstructs passage of fluid and catalyst. In this embodiment, the bands 154 include laterals 155 arranged to provide peaks 162 at an upper landing 163 and valleys 164 at a lower landing 165, but the peaks 162 and valleys 164 may be provided at the apex of a joint of just two bands 154. The layers A, B each include paired ribbons 142a, 142b. The lower landings 165 in upper ribbon 142a meet the upper landings 163 of lower ribbon 142b. A stabilizing strip 174 is disposed between upper landing 163 and lower landing 165. If paired ribbons 142a, 142b are cut out of a common piece of metal, a stabilizing strip 174 may be obviated. Ribbon 142a is disposed at a phase that is 180° out of phase to the phase of paired ribbon 142b. Other phase relationships may be used. Moreover, the axial spacing of a ribbon 142a is offset from the axial spacing of its paired ribbon 142b. Consequently, edges 158 of ribbon 142a and edges 158 of ribbon 142b may be parallel and may define a plane therebetween. The edges 158 of the laterals 155 and landings 163, 165 in ribbon 142a and the edges 158 of the laterals 155 and landings 163, 165 in ribbon 142b define openings 160 for the horizontal passage of fluid and catalyst. Edges of laterals 155 and landings 163, 165 in alternating upper ribbons 142a and alternating lower ribbons 142b define openings 161 for the vertical passage of fluid and catalyst. These openings 160, 161 are also defined by the faces 156 of the laterals 155 and upper and lower landings 163, 165. Dimples 176 may be provided in the bands 154. Although shown in laterals 155 near valleys 164, the dimples 176 may be disposed in lower landings 165. It is also contemplated that edges 158 of laterals 155 may be secured to each other in which case laterals 155 would cross each other. Moreover, although the ribbons 142a,b are preferably stacked horizontally in the central region 54 as seen in FIG. 4, the ribbons 142 may be arranged vertically in the central region 54 as seen in FIG. 4. FIG. 5 shows valleys 164 of lower ribbons 142b in layer A stacked on peaks 162 of upper ribbons 142a in layer B. An alternate arrangement can have the landings 163, 165 oriented in a vertical direction, or a direction parallel to the central axis of the vessel.

Figure 6:
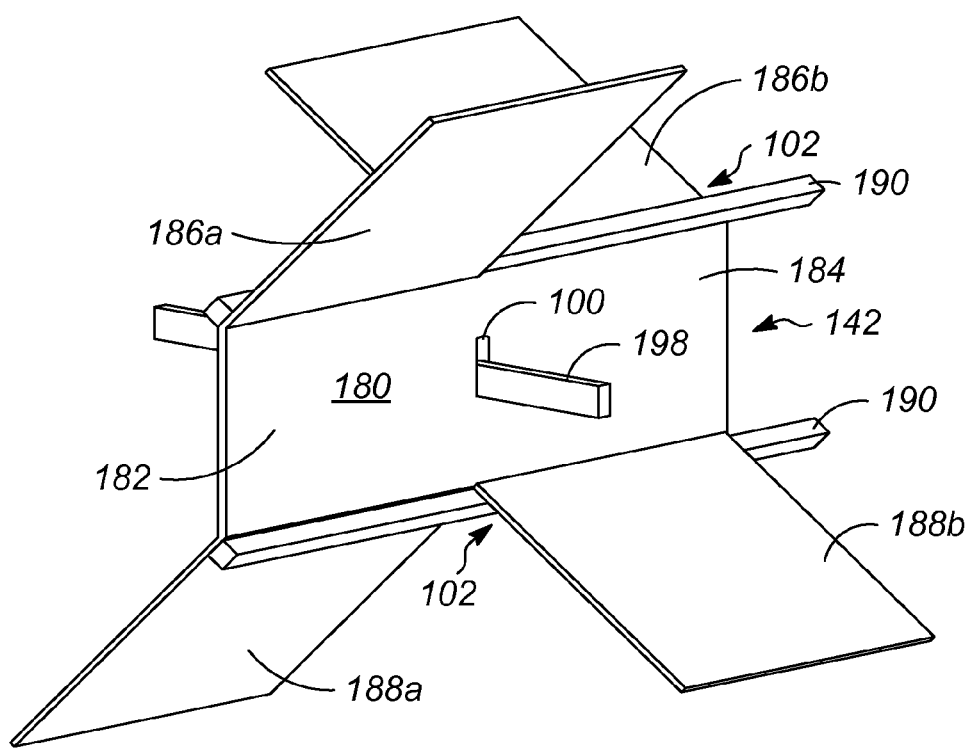
FIG. 6 shows a second example of a part of the reactor internals.

FIG. 6 is an enlarged partial perspective view of two segments 182, 184 of one ribbon 142. Upper tabs 186a, 186b of adjacent segments 182, 184, respectively, project from the standard strip 180 and may have opposite configurations and be angular to each other. Lower tabs 188a, 188b of adjacent segments 182, 184, respectively, project from standard strip 180 and may have opposite configurations and be angular to each other. Tie rods 198 extend through apertures 100 in standard strip 180 to secure ribbons 142 in an array. The tie rod 198 may be welded to the standard strip 180. Stabilizing strips 190 are seated in and secured to troughs 102 defined by upper tabs 186a, 186b and lower tabs 188a, 188b of adjacent segments 182, 184.

The vanes, or ribbon sections that are angled with respect to the central axis of the vessel are between 5° and 60° from the central axis. Preferably, the vanes or ribbon sections are angled between 40° and 50°, and with a most preferred angle of about 45°.

While FIGS. 5 and 6 provide examples of the reactor internals, the invention is not limited to these structures, but it is intended that the reactor internals comprise a configuration within the limits specified. For the purpose of this invention, the use of the term vane also refers to the section of the ribbons, 155 or 186 or 188, that is angled with respect to the central axis of the vessel.

While it is preferred to have the structured packing units affixed to one another, due to design considerations, a small spacer can be placed between adjacent units. However, the spacing of the adjacent units is to be less than 1 cm in the axial direction.

The reactor vessel 20 can includes a gas-solid separation system 74 for capturing small catalyst particles that can become entrained with the product gas.

In a particular embodiment, a reactor for the dehydrogenation of hydrocarbons comprises a reactor shell 20 having a generally cylindrical configuration and having an upper region 52, a central region 54 and a lower region 56, a catalyst inlet 62 disposed in the upper region 52 of the shell, a catalyst outlet 64 disposed in the lower region 56 of the shell, a process stream inlet 66 disposed in the lower region 56 of the shell, and a process stream outlet 68 disposed in the upper region of the shell 52, wherein the upper region 52 of the reactor shell has a greater diameter than the central region 54 of the reactor shell. The reactor includes a set of reactor internals 50 disposed within the central region 54 of the shell, wherein the reactor internals 50 are for guiding the flow of catalyst in a downward direction, while limiting axial back-mixing of the catalyst. The reactor internals 50 are designed to limit the flow rate of the catalyst through the reactor and to provide a means of distributing catalyst through the catalyst bed and to provide for some mixing of the catalyst in the radial and azimuthal directions. The reactor internals also prevent the creation and growth of gas bubbles within the bed. The reactor also includes a catalyst distributor 30 disposed in the upper region 52 of the shell and above the catalyst bed to provide a means to distribute catalyst over the catalyst bed. The reactor also includes a process stream distributor 32 disposed within the lower region 56 of the shell to distribute the process stream over the entire catalyst bed and to limit maldistribution of gas flow.

In this particular embodiment, the reactor includes a gas inlet port 72 disposed in the upper region 52 of the shell for admitting a quench fluid. The quench fluid provides for rapid cooling of the product stream. The reactor design also includes a gas-solid separation system disposed within the upper region 52 of the shell for recovering and returning entrained catalyst particles to the catalyst bed.

The reactor internals 50 comprise vanes for moving the catalyst in a radial or azimuthal direction as the catalyst flows downward. The vanes are angled between 30° and 60° from the central axis of the vessel 20.

By controlling the flow of the catalyst, and having a larger amount of catalyst flowing in the downward axial direction, a temperature profile along the axial direction can be established. This design promotes and even fluidized bed density distribution throughout the reactor and inhibits the formation of zones having catalyst voids.

The dehydrogenation process comprises contacting a hydrocarbon stream with a dehydrogenation catalyst at an elevated temperature. Dehydrogenation catalysts include noble metals on a support. One catalyst is platinum (Pt) on a support such as alumina. Another catalyst is gallium oxide ($Ga_2O_3$) on a support, such as alumina, silica, active carbon, or another refractory material. Other catalyst for dehydrogenation include chromic oxide ($Cr_2O_3$) on a support, molybdenum (Mo) on alumina ($Al_2O_3$), tin (Sn) promoted noble metals on a support, iron (Fe) and potassium (K) promoted chromic oxide, and copper (Cu) and copper chromite. Supports include zeolites, alumina, silica-aluminas, zirconia, silica, magnesia, carbon and other refractory materials. Other dehydrogenation catalyst include non-noble metal catalysts. In one embodiment, a preferred catalyst is a non-noble metal catalyst such as noble-metal free zirconia. The use of a noble-metal free catalyst saves on catalyst costs, and allows for flexible operation with a high catalyst circulation rate.

One embodiment of the invention comprises passing catalyst from a dehydrogenation catalyst distributor to the top of a catalyst bed in the dehydrogenation reactor. The catalyst flows downward under gravity through the reactor in the reaction section of the reactor. A hydrocarbon feedstream comprising paraffinic compounds is passed to a feedstream distributor disposed at the bottom of the catalyst bed. The hydrocarbon feedstream flows upward through the reactor and over the catalyst in the catalyst bed, to generate a product stream comprising olefins. The process stream is quenched in the upper part of the reactor vessel with a quench gas to reduce the temperature of the product stream. The quench gas can be any inert gas to lower the product stream temperature to inhibit further thermal reactions.

The catalyst flows down through the catalyst bed through vanes to guide the catalyst flow and to limit back-mixing of the catalyst in the axial direction. Other guides, such as packing grids, or stripper packing can be used within the catalyst bed.

The catalyst after passing through the catalyst bed is collected at the bottom of the reactor vessel. The catalyst is passed to a regeneration unit, and is preheated before passing into the regeneration unit. In an alternative, and preferred method, the catalyst is regenerated using additional fuel. The additional fuel combusts and raises the catalyst temperature leaving the regenerator without having to preheat the catalyst before returning the catalyst to the reactor.

The feedstream is heated before passing to the feedstream distributor. One embodiment for heating the feedstream comprises passing the product stream through a combined feed heat exchanger to preheat the feedstream and to further cool the product stream. The preheated feedstream is then heated to a desired feed inlet temperature between 450° C. and 550° C.

In one embodiment of the invention, the invention comprises a reactor for use in the dehydrogenation of hydrocarbons. The reactor includes a reactor shell, wherein the shell has a larger diameter than a normal reactor shell. The reactor shell includes an upper region, a central region, and a lower region. The reactor shell further includes a catalyst inlet disposed in the upper region, a catalyst outlet disposed in the lower region, a process stream inlet in the lower region, and a product stream outlet in the upper region. The reactor further includes in the central region of the reactor shell a set of reactor internals. The reactor internals comprise vanes for guiding the flow of catalyst in a downward direction and limit or restrict axial backmixing of the catalyst. As the reactor shell will have a larger diameter, the catalyst will need to be distributed and the reactor will include a catalyst distributor disposed above the catalyst bed, in the upper region, to uniformly distribute catalyst over the top of the catalyst bed. To limit local inhomogeneities, the process stream needs to be distributed over the broader area beneath the catalyst bed, and the reactor includes a process stream distributor disposed beneath the catalyst bed, and in the lower region of the reactor shell.

The reactor can further include a gas inlet port disposed in the upper region of the shell. The gas inlet port allows for the admission of a quench gas to cool the product stream after leaving the catalyst bed. The reactor shell can include a gas-solid separation system in the upper region of the reactor shell to separate catalyst particles carried from the catalyst bed by the product stream.

The present invention provides for a much more favorable temperature profile in the axial direction, or the process stream flow direction, over current technologies that utilize a plurality of reactors with reactor interheaters. The reactors have falling temperature profiles with respect to the direction of hydrocarbon flow. This presents improvements over an adiabatic fixed bed reactor system operated in a swing mode where there is a shifting of stream between fixed bed reactors and the reactor beds are heated and regenerated in between reaction cycles. This also is an improvement over a fully back-mixed fluidized bed, as a back-mixed bed would have a flat temperature profile, and the process stream would have a longer exposure time to the high temperatures.

With this design a rising temperature profile, relative to the process stream flow direction, is created. This allows for partial conversion at lower temperature with the inlet stream and where the reaction equilibrium can still be favorable due to relatively low concentrations of olefins. As the process stream encounters higher temperatures, the equilibrium shifts favorably, while limiting the high temperature contact time. A greater amount of catalyst can flow through the reactor, and the catalyst can be heated to supply the heat and flow more slowly through the reactor to sustain the endothermic dehydrogenation reaction.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for dehydrogenation of hydrocarbons comprising:
   flowing a catalyst in a catalyst bed, in a downward direction, through a dehydrogenation reactor, wherein the catalyst is added at a catalyst inlet temperature of at least 650° C.; and
   flowing a paraffinic feedstream in an upward direction through the catalyst bed, thereby contacting the paraffinic feedstream with the catalyst at dehydrogenation reaction conditions, thereby generating a product stream, wherein the paraffinic feedstream is added at a paraffinic feedstream inlet temperature of at least 400° C. and less than 600° C., wherein the paraffinic feedstream travels in an upward direction through the dehydrogenation reactor, providing for a substantially countercurrent flow of catalyst and paraffinic feedstream and wherein the paraffinic feedstream inlet temperature is between 100° C. and 250° C. below the catalyst inlet temperature, wherein the catalyst bed includes a packing grid comprising multiple layers of ribbons, wherein the ribbons refer to metal strips formed and angled relative to each other and the layers are stacked to be in contact with neighboring layers.

2. The process of claim 1 further comprising quenching the product stream.

3. The process of claim 2 wherein the quenching of the product stream comprises adding a portion of a cooled product stream.

4. The process of claim 1 further comprising passing the catalyst from a regenerator to a catalyst distributor disposed above the catalyst bed.

5. The process of claim 1 further comprising collecting the catalyst at the bottom of the reactor to generate a return catalyst stream.

6. The process of claim 5 further comprising passing the return catalyst stream to a catalyst regenerator.

7. The process of claim 1 further comprising passing the paraffinic feedstream to a feedstream distributor disposed beneath the catalyst bed prior to flowing the paraffinic feedstream over the catalyst bed.

8. The process of claim 1 wherein the catalyst is passed to the top of the catalyst bed at a temperature between 650° C. and 800° C.

9. The process of claim 8 wherein the catalyst is passed to the top of the catalyst bed at a temperature between 650° C. and 750° C.

10. The process of claim 1 wherein the paraffinic feedstream is at a temperature between 450° C. and 550° C.

11. A process for dehydrogenation of hydrocarbons comprising:
    passing catalyst from a dehydrogenation reactor catalyst distributor to a dehydrogenation reactor, wherein the catalyst is admitted at a catalyst inlet temperature of at least 650° C.;
    flowing the catalyst in a catalyst bed, in a downward direction, through the dehydrogenation reactor, wherein the catalyst bed includes a packing grid comprising multiple layers of ribbons, wherein the ribbons refer to metal strips formed and angled relative to each other and the layers are stacked to be in contact with neighboring layers;
    collecting the catalyst at the bottom of the dehydrogenation reactor to generate a return catalyst stream;
    passing a paraffinic feedstream to a feedstream distributor disposed beneath the catalyst bed, wherein a paraffinic feedstream inlet temperature is at least 400° C. and no more than 600° C., and wherein the paraffinic feedstream inlet temperature is between 100° C. and 250° C. below the catalyst inlet temperature;
    flowing the paraffinic feedstream in an upward direction through the catalyst bed, thereby contacting the paraffinic feedstream with the catalyst, thereby generating a product stream, wherein the paraffinic feedstream travels in an upward direction through the dehydrogenation reactor, providing for a substantially countercurrent flow of catalyst and paraffinic feedstream; and
    quenching the product stream.

12. The process of claim 11 further comprising passing the product stream through a combined feed exchanger to preheat the paraffinic feedstream and cool the product stream.

13. The process of claim 11 wherein the catalyst is returned from a regenerator at a temperature between 650° C. and 750° C.

14. The process of claim 11 wherein the paraffinic feedstream is introduced to the dehydrogenation reactor at a temperature between 400° C. and 550° C.

15. The process of claim 11 wherein the catalyst is guided in the downward direction through the use of reactor internals to guide the catalyst in the downward flow.

16. The process of claim 11 wherein the dehydrogenation reactor has a reactor product outlet pressure between 20 kPa (absolute) and 400 kPa (absolute).

17. A process for dehydrogenation of hydrocarbons comprising:
passing catalyst from a dehydrogenation reactor catalyst distributor to a dehydrogenation reactor, wherein a catalyst inlet temperature is at least 650° C.;
flowing the catalyst in a catalyst bed, in a downward direction, through the dehydrogenation reactor, wherein the catalyst bed includes a packing grid comprising multiple layers of ribbons, wherein the ribbons refer to metal strips formed and angled relative to each other and the layers are stacked to be in contact with neighboring layers;
collecting the catalyst at the bottom of the dehydrogenation reactor to generate a return catalyst stream;
regenerating and heating the catalyst in a catalyst regenerator to create a return catalyst stream;
passing a paraffinic feedstream to a feedstream distributor disposed beneath the catalyst bed, wherein the temperature of the paraffinic feedstream is at least 100° C. below the catalyst inlet temperature;
flowing the paraffinic feedstream in an upward direction through the catalyst bed, thereby contacting the paraffinic feedstream with the catalyst, thereby generating a product stream, wherein the paraffinic feedstream travels in an upward direction through the dehydrogenation reactor, providing for a substantially countercurrent flow of catalyst and paraffinic feedstream; and
quenching the product stream;
wherein a substantially uniform temperature difference is maintained between the catalyst and the process stream as the catalyst and the process stream flow through the dehydrogenation reactor dehydrogenation reactor and wherein the process stream refers to a reaction mixture in the dehydrogenation reactor.

18. The process of claim 17 wherein the paraffinic feedstream has an inlet temperature between 100° C. and 250° C. below the catalyst inlet temperature.

19. The process of claim 17 wherein the paraffinic feedstream has an inlet temperature between 150° C. and 200° C. below the catalyst inlet temperature.

* * * * *